US00PP17841P2

(12) United States Plant Patent
Meilland

(10) Patent No.: US PP17,841 P2
(45) Date of Patent: Jul. 3, 2007

(54) FLORIBUNDA ROSE PLANT NAMED 'MEIDELWEIS'

(50) Latin Name: *Rosa hybrida*
Varietal Denomination: Meidelweis

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 324 days.

(21) Appl. No.: 11/002,621

(22) Filed: Dec. 3, 2004

(51) Int. Cl.
*A01H 5/00* (2006.01)

(52) U.S. Cl. ..... Plt./141
(58) Field of Classification Search ..... Plt./141, Plt./142, 143, 144, 149
See application file for complete search history.

(56) References Cited

U.S. PATENT DOCUMENTS

PP8,143 P * 2/1993 Austin ..... Plt./107

* cited by examiner

*Primary Examiner*—Howard J. Locker
(74) *Attorney, Agent, or Firm*—Buchanan & Ingersoll PC

(57) ABSTRACT

A new and distinct variety of rose plant of the Floribunda Class is provided which abundantly forms attractive pure white blossoms possessing a large number of petals and a configuration similar to that of an old-fashioned rose. The petals initially bear some pink coloration at the margins that is lost as the blossoms fully mature. The growth habit is compact and bushy. Very ornamental dark green and glossy foliage is formed that contrasts nicely with the white blossom coloration. The fragrance of the blossoms is distinctive and is reminiscent of citrus. The new variety is particularly well suited for forming attractive ornamentation in the landscape.

3 Drawing Sheets

Botanical/commercial classification: *Rosa hybrida*/Floribunda Rose Plant.
Varietal denomination: cv. 'Meidelweis'.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) of the new variety was the product of the cross of the 'Kimono' variety (non-patented in the United States) and the 'AUSreef' variety (U.S. Plant Pat. No. 8,143). The 'AUSreef' variety sometimes is known as the 'Sharifa Asma' variety. The male parent (i.e., the pollen parent) was the 'Delge' variety (non-patented in the United States). The 'Delge' variety sometimes is known as the 'Centenaire de Lourdes. The parentage of the new variety can be summarized as follows:

('Kimono'×'AUSreef')×'Delge'.

The seeds resulting from the above pollination were sown and small plants were obtained which were physically and biologically different from each other. Selective study resulted in the identification of a single plant of the new variety.

It was found that the new Floribunda rose plant of the present invention possesses the following combination of characteristics:

(a) exhibits a compact and bushy growth habit;

(b) forms in abundance attractive pure white blossoms that initially include some pink coloration at the margins prior to full maturity possessing a large number of petals and a configuration similar to that of an old-fashioned rose which display a citrus fragrance, (c) forms very ornamental dark green and glossy foliage, and (d) is particularly well suited for forming attractive ornamentation in the landscape.

The pink coloration at the margins of the petals commonly is lost as the blossoms fully mature. The fragrance of the blossoms is distinctive and is reminiscent of citrus.

The new variety well meets the needs of the horticultural industry. It is particularly well suited for enhancing the appearance of parks and gardens.

The new variety can be readily distinguished from its ancestors. More specifically, the 'Kimono' variety forms blossoms that are salmon-pink in coloration, the 'AUSreef' variety forms blossoms that are pale pink in coloration that fade to pinkish white, and the 'Delge' variety forms blossoms that are soft rose in coloration.

The new variety has been found to undergo asexual propagation at Le Cannet des Maures, Var, France by a number of routes including budding, grafting, and the rooting of cuttings. Asexual propagation by the above-mentioned methods as performed at such location has shown that the characteristics of the new variety are strictly transmissible from one generation to another. Accordingly, the new variety undergoes asexual propagation in a true to type manner.

The new variety has been named the 'Meidelweis' and will be marketed under the BOLERO and ROMANTICA trademarks.

BRIEF DESCRIPTION OF THE PHOTOGRAPHS

The accompanying photographs show as nearly true as it is reasonably possible to make the same in color illustrations of this character typical specimens of the new variety. The rose plants of the new variety were two years of age and was photographed during June 2003 while growing on *Rosa froebelli* rootstock at West Grove, Pa. U.S.A.

DETAILED DESCRIPTION

Figure 1:
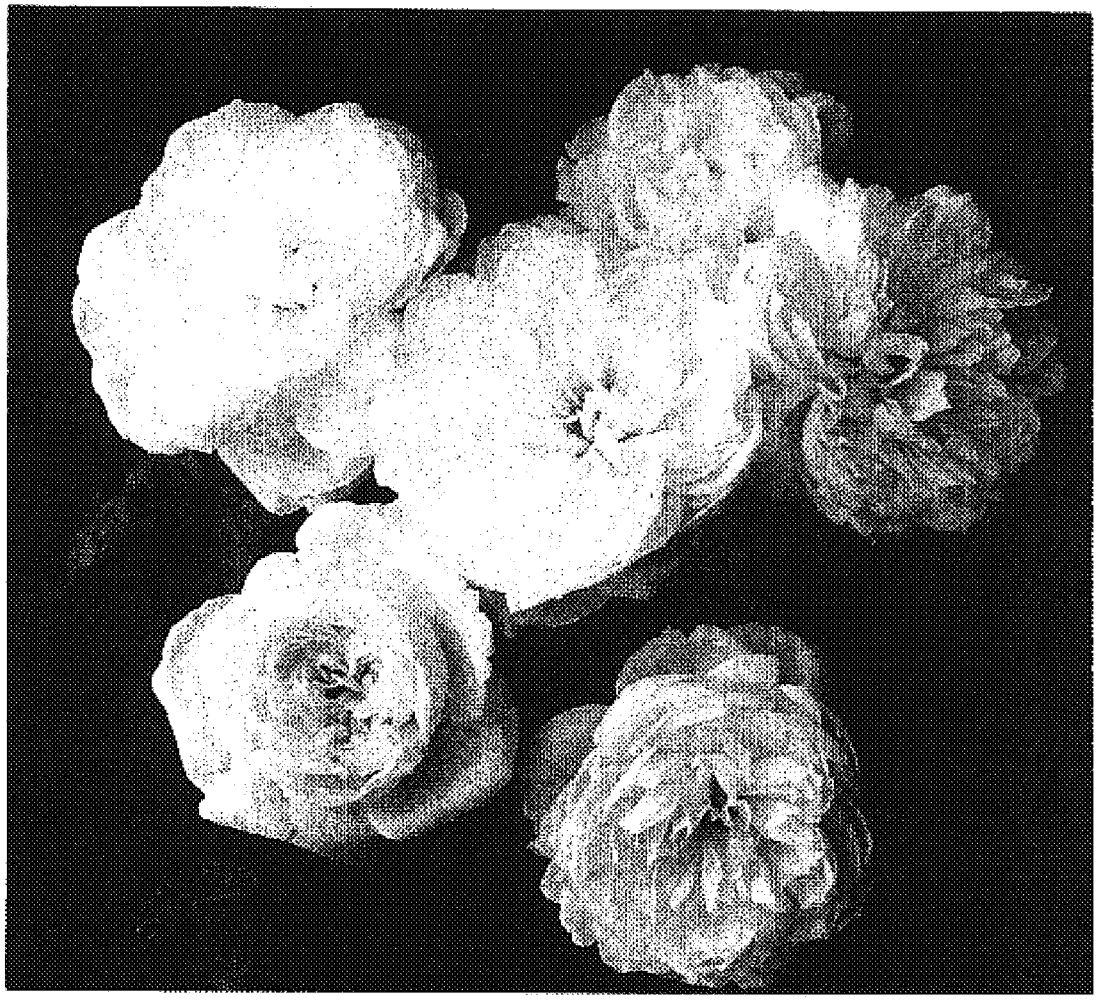
FIG. 1 illustrates a cluster of blossoms of the new variety. Some blossoms such as the one at the lower left are recently opened and display a hint of pink coloration at the margins.
Figure 2:
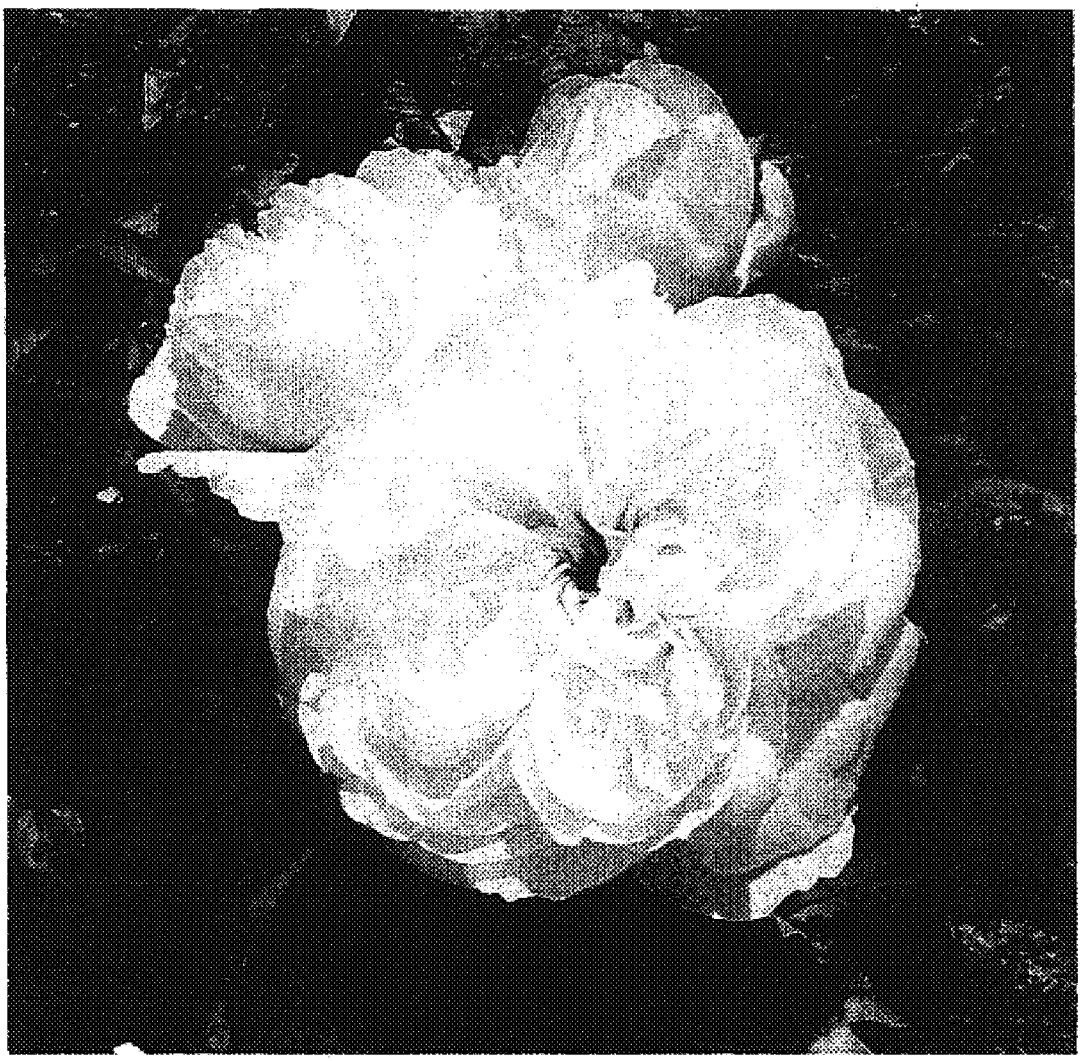
FIG. 2 illustrates further blossoms as well as the attractive dark green glossy foliage.
Figure 3:
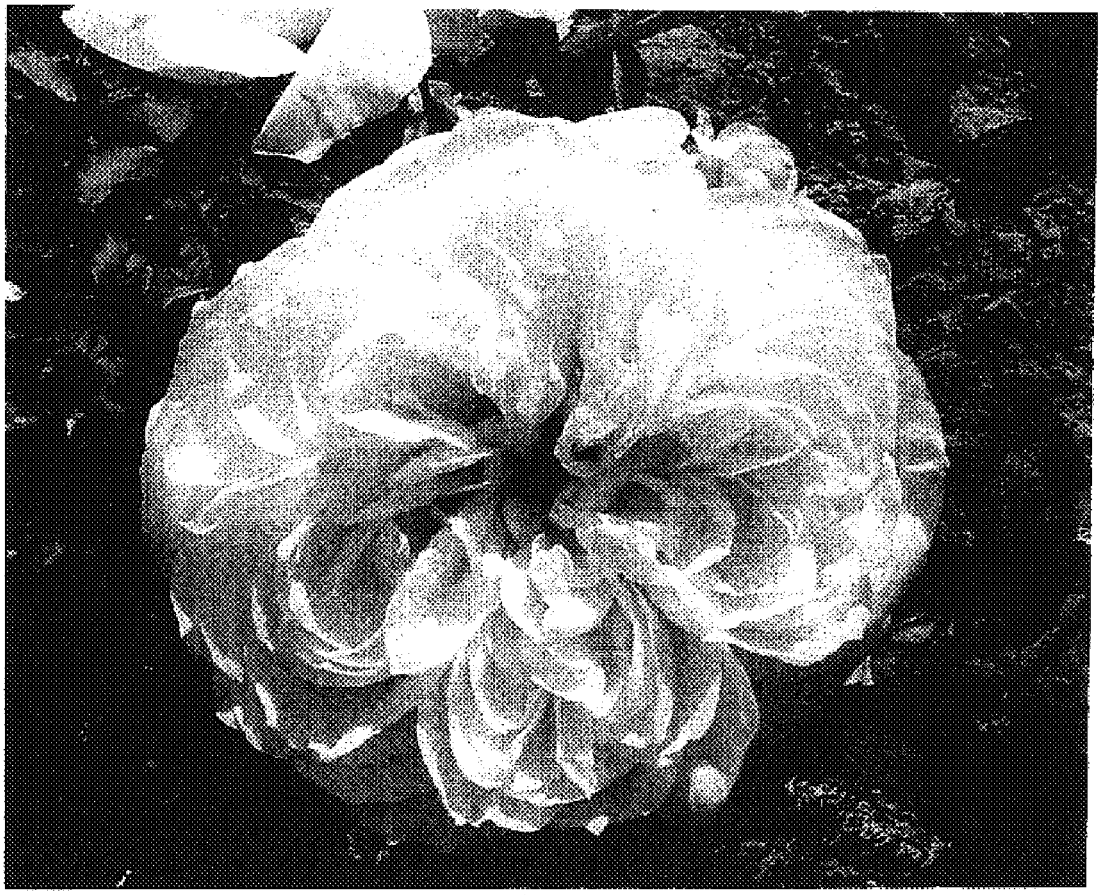
FIG. 3 illustrates an additional fully-opened mature blossom that well shows the old-fashioned rose configuration together with some foliage.

The chart used in the identification of the colors is that of The Royal Horticultural Society (R.H.S. Colour Chart). The description is based on the observation of two year-old specimens of the new variety which were observed during June while growing outdoors on *Rosa froebelli* rootstock at West Groove, Pa. U.S.A.

Class: Floribunda.

Plant:

*Height.*—Approximately 70 to 90 cm on average at the end of the growing season.

*Spread.*—Approximately 60 to 70 cm on average.

*Growth habit.*—Compact and bushy.

*Stem length.*—Commonly less than 45 cm.

Branches:

*Color.*—Young stems: light green, Green Group 143C, and tinged with reddish coloration. Adult wood: medium green, Green Group 137D.

*Thorns.*—Size: medium, approximately 8 mm in length, and the base commonly is approximately 5 mm in length and approximately 2 mm in width. Quantity: fairly numerous and commonly approximately 40 to 45 per stem. Color: greenish on young stems, and on mature wood commonly Orange-Red Group 34D changing to Greyed-Yellow Group 160B at the point.

Leaves:

*Arrangement.*—Alternate and odd-pinnately compound.

*Petioles.*—Upper surface: striped with reddish coloration on the young foliage and medium green on the adult foliage with more or less glandular edges. Under surface: rarely exhibits some small prickles.

*Stipules.*—Adnate, pectinate, and very large and linear with the length commonly being approximately 14 mm and the width approximately 3 mm.

*Leaflets.*—Number: 3, 5, and 7. Shape: generally oval. Margin: with single and regular serration. General appearance: dense, glossy, dark green, and very ornamental. Texture: coriaceous. Color (young foliage): Upper surface: light green, Green Group 137B and tinged with Red-Purple Group 59A at the edges and somewhat throughout. Under surface: light green, Yellow-Green Group 148C and tinged with Red-Purple Group 59A at the edges and somewhat throughout. Color (adult foliage): Upper surface: Green Group 137A. Under surface: lighter green, Yellow-Green Group 148C.

Inflorescence:

*Number of flowers.*—Typically approximately 2 or 3 per stem, with the flower productivity being good and generally corresponding to that of better-flowering Floribunda varieties.

*Peduncle.*—Commonly approximately 5 cm in length, approximately 9 mm in diameter, near Yellow-Green Group 144B in coloration, and more or less glandular commonly with some small prickles or hairs.

*Sepals.*—Five in number, approximately 27 mm in length on average, approximately 7 mm in width on average, the upper surface is tomentose, greenish and widely tinged with reddish coloration, and bears foliar extensions, and the under surface is Yellow-Green Group 144A and is more or less tinged with coloration of Red-Purple Group 60A, and commonly also possesses foliage extensions. There commonly are approximately 5 foliar extensions per flower that commonly measure approximately 5 mm×1 mm.

*Buds.*—Shape: generally globular. Size: large. Length: approximately 2.5 to 3 cm on average. Color (upper surface): Red Group 56D at the margins, White Group 155D at the middle, and Yellow Group 3B at the base with the external petals commonly being somewhat lighter. Color (under surface): Red Group 56D at the margins, White Group 155D at the middle, and Yellow Group 3B at the base with the external petals commonly being somewhat lighter.

*Flower.*—Shape: cup-shaped at the middle and somewhat flat at the perimeter. Diameter: approximately 7 to 8 cm on average when fully open. Color when opening begins: Upper surface: Red Group 56D at the margins, White Group 155D at the middle, and Yellow Group 3B at the base with the external petals commonly being somewhat lighter. Under surface: Red Group 56D at the margins, White Group 155D at the middle, and Yellow Group 3B at the base with the external petals commonly being somewhat lighter. Color when blooming: Upper surface: Red Group 56D at the margins, White Group 155D at the middle, and Yellow Group 3B at the base with the external petals commonly being somewhat lighter. Under surface: Red Group 56D at the margins, White Group 155D at the middle, and Yellow Group 3B at the base with the external petals commonly being somewhat lighter. Color at end of blooming: Upper surface: White Group 155D from the margins to the base, and Yellow Group 3B at the base with the external petals commonly being somewhat lighter. Under surface: White Group 155D from the margins to the base, and Yellow Group 3B at the base with the external petals commonly being somewhat lighter. Stability of coloration: the pink coloration that is initially present at the margins of the petals is lost as the blossoms fully mature. Petal configuration: rounded. Petal number: ranges widely from approximately 140 to 160 on average under typical growing conditions. Petal arrangement: as an old-fashioned rose. Fragrance: reminiscent of citrus. Stamen number: commonly approximately 15 to 20 on average. Filaments: yellowish in coloration. Pollen: near Yellow-Orange Group 21C in coloration, and generally moderate in quantity. Anthers: ochre in coloration. Pistil number: commonly approximately 40 to 50 on average. Styles: greenish in coloration with a fuchsia tip. Stigmas: ochre in coloration. Lastingness: long, the blossoms commonly last 8 days or more on the plant, and approximately 6 days when cut and placed in a vase. The longevity of the blossoms is greatly influenced by the environmental conditions that are encountered. Petal drop: the petals commonly detach cleanly following full maturity. Receptacle: medium green, smooth, and in longitudinal section in the shape of a pitcher. Hips: generally ovoid in shape, commonly approximately 10 mm in length on average and approximately 8 mm in width on average. Seeds: commonly approximately 1 to 6 per hip, approximately 3 mm in length on average, and dark brown in coloration.

Development:

*Vegetation.*—Strong.

*Blooming.*—Abundant.

*Aptitude to bear fruit.*—Not overly abundant fruit formation has been observed.

*Resistance to diseases.*—Very good with respect to Powdery Mildew (*Sphaerotheca pannosa*) and Black Spot (*Dipolcarpon rosae*).

*Aptitude to be forced.*—Good.

*Winter hardiness.*—Hardy down to U.S.D.A. Hardiness Zone No. 5B, and can survive colder zones when provided with winter protection.

The new 'Meidelweis' variety has not been observed under all possible environmental conditions to date. Accordingly, it is possible that the phenotypic expression may vary somewhat with changes in light intensity and duration, cultural practices, and other environmental factors without variance of the genotype.

I claim:

1. A new and distinct Floribunda rose plant characterized by the following combination of characteristics:

(a) exhibits a compact and bushy growth habit, (b) forms in abundance attractive pure white blossoms that initially include some pink coloration at the margins prior to full maturity possessing a large number of petals and a configuration similar to that of an old-fashioned rose which display a citrus fragrance, (c) forms very ornamental dark green and glossy foliage, and (d) is particularly well suited for forming attractive ornamentation in the landscape;

substantially as herein shown and described.

* * * * *